US00PP10790P

United States Patent [19]

Zaiger et al.

[11] Patent Number: Plant 10,790

[45] Date of Patent: Feb. 16, 1999

[54] CHERRY TREE NAMED 'ROYAL RAINIER'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 959,628

[22] Filed: Oct. 22, 1997

[51] Int. Cl.[6] ..... A01H 5/00

[52] U.S. Cl. ..... Plt./37

[58] Field of Search ..... Plt./37

*Primary Examiner*—Howard J. Locker
*Assistant Examiner*—Melissa L. Kimball

[57] ABSTRACT

A new and distinct variety of cherry tree (*Prunus avium*) with the following unique combination of desirable features that are outstanding in a new variety:

1. Fruit with good flavor and eating quality.
2. Firm fruit with good handling and shipping qualitites.
3. Heavy and regular production of medium to large size fruit.
4. The ability of the fruit to hold firm on the tree 6 to 7 days after maturity (shipping ripe).
5. Vigorous, upright growth.
6. Fruit with yellowish-white skin that has an attractive red blush when exposed to the sun.

1 Drawing Sheet

ORIGIN OF THE VARIETY

The new and distinct variety of cherry tree named 'Royal Rainier' was originated as an open pollinated seedling of 32G153. The selection 32G153 originated as an open pollinated seedling of Stella Cherry (non-patented). A large number of these open pollinated seedlings were grown under careful observation by us in our experimental orchard located near Modesto, Calif. One such seedling, which is the present variety, being especially desirable for its fruit quality and heavy production, was selected for asexual reproduction and commercialization.

ASEXUAL REPRODUCTION OF THE VARIETY

Asexual reproduction of the new and distinct variety of cherry tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of cherry tree is of large size, vigorous, upright growth and a regular and productive bearer of medium to large size fruit with good flavor and eating quality. The fruit is further characterized by its yellowish-white skin having an attractive red blush when exposed to the sun, firm flesh, the ability to hold firm on the tree 6 to 7 days after maturity (shipping ripe) and ripening approximately 5 days before the Stella Cherry (non-patented).

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a fruit divided in it suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of cherry tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Productivity.*—Productive.
- *Bearer.*—Regular.
- *Density.*—Medium dense.

Trunk:
- *Size.*—Large.
- *Texture.*—Medium stocky, roughens with maturity.
- *Color.*—Light brown to brown (7-D-5) to (7-E-5).

Branches:
- *Size.*—Medium.
- *Texture.*—Smooth to medium rough, varies with age of growth.
- *Lenticels.*—Medium number. Large size.
- *Color.*—Grayish brown to brownish beige (6-D-3) to (6-E-3), varies with age of growth.

Leaves:
- *Size.*—Large. Average length 5½". Average width 2¼".
- *Form.*—Obovate with acuminate tip.
- *Margin.*—Serrate.
- *Thickness.*—Medium.
- *Surface.*—Smooth.
- *Petiole.*—Average length 1½". Medium thickness.
- *Glands.*—Reniform. Size — large. Number varies from 1 to 4. Average number 2. Located primarily on the upper portion of the petiole.
- *Color.*—Upper surface — green to deep green (27-E-4) to (27-E-8). Lower surface — dull green to grayish-green (28-D-4) to (28-D-6).

Flower buds:
- *Size.*—Large.
- *Length.*—Medium.
- *Form.*—Plump.

Flowers:

*Size.*—Large.

*Pollen.*—Present.

*Blooming period.*—Date of first bloom: Mar. 21, 1996. Date of full bloom: Mar. 27, 1996. Varies slightly with climatic conditions.

*Color.*—White.

*Flowers per cluster.*—Highly variable, multi-flowered.

*Pollination requirements.*—Requires pollinator, not self-fertile.

Fruit:

*Maturity when described.*—Firm ripe.

*Date of first picking.*—May 17, 1996.

*Date of last picking.*—May 22, 1996. Varies slightly with climatic conditions.

*Size.*—Medium to large. Comparatively uniform. Average diameter axially 1". Average transversely in suture plane 1⅛".

*Form.*—Relatively uniform, globose to slightly oblate.

*Suture.*—Shallow, extends from base to apex. Relatively smooth.

*Ventral surface.*—Nearly rounded.

*Apex.*—Rounded to slight depression.

*Base.*—Retuse.

*Cavity.*—Rounded. Average depth ⅛". Average breadth 3/16".

Flesh:

*Ripens.*—Relatively even.

*Texture.*—Firm.

*Fibers.*—Small and tender.

*Eating quality.*—Good.

*Flavor.*—Good, mild, sweet, good balance between acid and sugar.

*Color.*—White to orange white (5-A-1) to (5-A-2). Pit cavity — light yellow to yellow (3-A-5) to (3-A-6).

Skin:

*Thickness.*—Medium.

*Texture.*—Medium.

*Down.*—Wanting.

*Tendency to crack.*—None during dry weather. Some slight cracking during wet weather, varies with stage of fruit maturity.

*Color.*—Pale yellow to light yellow (4-A-3) to (4-A-4). Where fruit is a red to dark red blush (11-B-6) to (11-C-8).

Stem of fruit:

*Length.*—Average length 1¾".

*Thickness.*—Medium.

Stone:

*Type.*—Semi-freestone, adheres to flesh slightly along ventral edge.

*Size.*—Average length ½". Average width ⅜". Average thickness ¼".

*Form.*—Somewhat globose.

*Base.*—Slightly rounded.

*Apex.*—Rounded to slight apical point.

*Surface.*—Smooth, with slight ridges near suture line.

*Sides.*—Equal.

*Tendency to split.*—None.

*Color.*—Light tan to tan (5-B-4) to (5-B-5).

Use: Dessert. Market, local and long distance.

Keeping quality: Exceptional, low occurence of bruising.

Shipping quality: Good.

Disease resistance: No susceptibility to diseases observed to date.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of cherry tree substantially as illustrated and described, characterized by its large size, vigorous upright growth, being a productive and regular bearer of medium to large size fruit that has the ability to remain firm on the tree 6 to 7 days after maturity (shipping ripe); the fruit is further characterized by its yellowish-white skin with an attractive red blush where exposed to the sun, it has good flavor and eating quality and ripens approximately 5 days before Stella Cherry (non-patented).

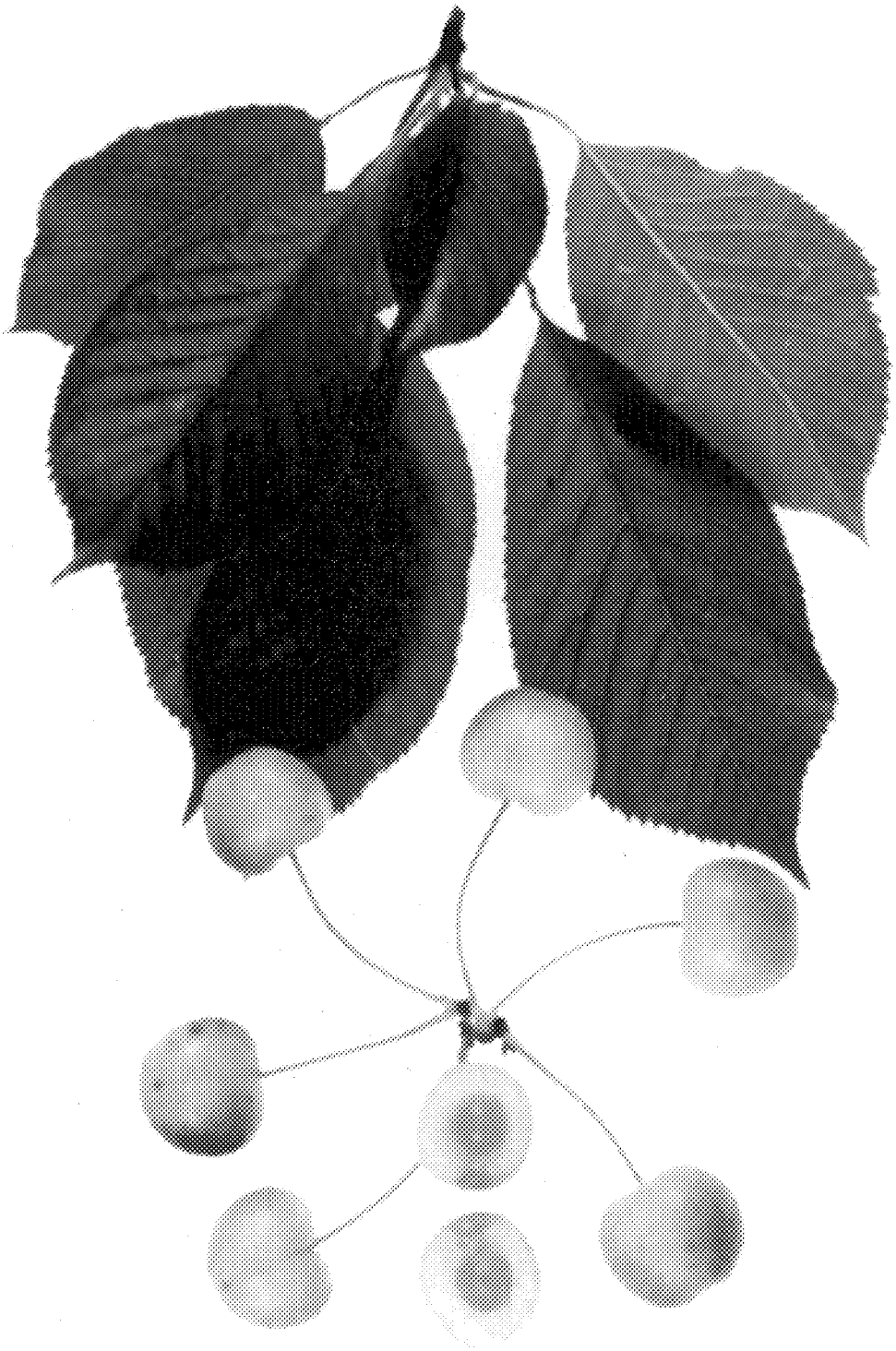

* * * * *